United States Patent
Chu et al.

(10) Patent No.: US 6,476,238 B1
(45) Date of Patent: Nov. 5, 2002

(54) PURIFICATION METHOD FOR OBTAINING HIGH-PURITY PMDA

(75) Inventors: Shiao-Jung Chu; Chien-Liang Hwang, both of Hsinchu (TW)

(73) Assignee: Chinese Petroleum Corp. (TW)

( * ) Notice: Subject to any disclaimer, the term of this patent is extended or adjusted under 35 U.S.C. 154(b) by 0 days.

(21) Appl. No.: 09/855,429

(22) Filed: May 16, 2001

(51) Int. Cl.⁷ ..................... C07D 307/77; C07D 407/02
(52) U.S. Cl. ..................................... 549/299
(58) Field of Search ......................... 549/299

(56) References Cited

FOREIGN PATENT DOCUMENTS

JP          07188242      *  7/1995

* cited by examiner

*Primary Examiner*—T. A. Solola
(74) *Attorney, Agent, or Firm*—Powell Goldstein Frazer & Murphy

(57) ABSTRACT

A purification method for obtaining high-purity PMDA. The method controls temperatures of cyclone separators in a series to separate PMDA and other by-products of different sublimation temperatures. High-purity PMDA is collected in the first cyclone separator, and no other purification steps are needed.

15 Claims, No Drawings

PURIFICATION METHOD FOR OBTAINING HIGH-PURITY PMDA

BACKGROUND OF THE INVENTION

1. Field of Invention

The present invention relates to a purification method for obtaining high-purity pyromellitic dianhydride (PMDA). More particularly, the present invention relates to using a temperature-controllable cyclone separator to obtain high-purity PMDA.

2. Description of Related Art

Polyimide (Pl) is a kind of high-performance engineering polymer. Polyimide can be used as an insulating film for components of electro-machines and microelectro-machines. It also can be used as a soft substrate for semiconductors. PMDA is the monomer of Pl thus the required purity of PMDA is very high.

Traditional purification processes for PMDA are extracted by solvent or purified by crystallization. Furthermore, the PMDA obtained is a very fine powder, therefore it is not convenient to use PMDA. Moreover, the purification process is complicated and produces effluent that needs to be handled. The waste effluent treatment causes a lot of problems.

For improving these disadvantages described above, the more recent developed method is to use desublimation method to refine the powdered PMDA product. Most methods disclosed in patents utilize the difference of dew point between PMDA and other components to separate the PMDA. For example, in JP 8-59668, a shell and tube heat exchanger was applied to purify PMDA. PMDA vapor contained stream, which is produced from a PMDA synthesis reactor or by heated crude PMDA, is passed through the tube of heat exchanger while a coolant is pass through the shell side counter currently. The temperature of outlet gases is cooled by coolant, and the resultant solids and gases are separated because sublimation temperatures of each component of outlet gases are different. However, if the outlet temperature is deviated from the set temperature slightly, a lot of powder will nucleate on the tube wall of the separator and block the tube.

Another method is to cool the outlet gases by quenching air to obtain PMDA powder such as described in JP 61-215352. Although bigger crystal of PMDA can be obtained by this method, impurities are often encompassed in PMDA crystals. Therefore, high purity of PMDA is not easy to obtain.

Using a bag filter to collect PMDA powder and performing succeeding purification steps is another method to purify PMDA, but water is often accompanying in product, therefore the resulting PMDA agglomerates powder always block the filter of the bag. Still another method is to use scrubbers to wash PMDA powder by using water to collect PMDA powder, then PMDA powder is dehydrated and purified.

There are some other pertinent patents such as JP 07188242, JP 0518473, JP 05078367, JP 63010790, JP 62093291, JP 01186839, JP 03294272, JP 59199683, Ger. Offen DE 87-3732-0747, and Ger. Offen DE 3501371, etc. Some of these patents utilize the desublimation method to purify PMDA. Some of these patents utilize organic solvents to extract PMDA, and then recrystallization is used to purify PMDA. The organic solvents used are a mixture of acetone, o-xylene and cyclohexane, or benzonitrile. Some of these patents hydrolyze PMDA to pyromellitic acid (PMA), then perform dehydration reaction to gain purified PMDA.

SUMMARY OF THE INVENTION

The invention provides a method for producing high-purity PMDA with larger size crystals.

This invention provides a purification method for obtaining high-purity PMDA. A reactor outlet is connected with an inlet of a first cyclone separator in series. The temperature of the reactor outlet is higher than a sublimation temperature of PMDA. The temperature of the first cyclone separator is lower than the sublimation temperature of PMDA and higher than that of by-products. Vapors of the PMDA and the by-products are directed to flow from the reactor outlet to the inlet of the first cyclone separator at a flow rate to obtain high-purity PMDA.

A temperature of the reactor outlet is, about 245 to about 255° C. The first cyclone separator has a temperature of about 165 to about 210° C. Furthermore, more than one cyclone separator can also be connected to the first cyclone separator in a series. A temperature of these succeeding cyclone separators is lower than sublimation temperatures of the by-products.

Therefore, this invention provides a very simple purification method for obtaining high-purity PMDA. Only one simple purification step can obtain high-purity PMDA (purity>99.0%). The complicated purification steps are largely simplified in this invention. The cost of producing high-purity PMDA is also largely decreased. Therefore, this invention is very suitable to be applied in mass-production of high-purity PMDA.

DESCRIPTION OF THE PREFERRED EMBODIMENTS

This invention provides a purification method for obtaining high-purity PMDA.

PMDA is generally obtained by oxidizing 1,2,4,5-tetramethyl benzene (durene). Thus some by-products result from incomplete oxidation of durene, for example, only parts of the methyl groups of durene are oxidized to —COOH or —CHO. Some by-products result from over oxidation of durene; for example, some carboxylic acids or aldehydes with smaller molecular weight are obtained by oxidation-fragmentation of durene. Since physical properties of these by-products are similar to PMDA, high-purity PMDA is not easy to obtain.

This invention provides a purification method of PMDA. Utilizing the different sublimation temperature between PMDA and by-products, PMDA is purified. The sublimation temperature, about 240° C., of PMDA is highest among the products of oxidizing durene. Therefore two to three cyclone separators are connected in an order of decreasing temperature, wherein the outlet of the first cyclone separator is connected to the inlet of the second cyclone separator and the outlet of the second cyclone separator is connected to the inlet of the third cyclone separator. The temperature of the first cyclone separator is slightly lower than the sublimation temperature of PMDA, and the temperatures of other cyclone separators after the first one is lower than the sublimation temperatures of other by-products.

Since the temperature of the first cyclone separator is slightly lower than the temperature of the sublimation temperature of PMDA, PMDA vapor condenses into PMDA powder and drop on the bottom of the first cyclone separator when PMDA and other by-products enter the first cyclone separator. Nevertheless, vapors of other by-products with lower sublimation temperatures (<180° C.) can pass the first cyclone separator to enter the following cyclone separators. These vapors of the by-products either condense into powder to drop on the bottom of the following cyclone separators or eject from the outlet of the last cyclone separator. Larger than 99.0% purity of PMDA powder can be collected in the first cyclone separator.

The temperature of the reactor outlet is higher than the sublimation temperature of PMDA. The temperature of the reactor outlet is, for example, about 245–255° C. The operating temperature of the first cyclone separator is lower than the sublimation temperature of PMDA and higher than the sublimation temperatures of other by-products. The operating temperature of the first cyclone separator is preferred to be about 165–210° C. and even more desired to be about 175–185° C. The operating temperatures of the following cyclone separators are gradually decreased. The operating temperatures of the following cyclone separators are preferred to be about 100–180° C. and more desired to be about 110–165° C. The space flow rate of gases are preferred to be about 3,000–12,000 $hr^{-1}$ and more desired to be about 4,000–8,000 $hr^{-1}$. The gases flow rate at the inlet of cyclone separators are preferred to be lower than about 20 m/s and more desired to be about 15 m/s.

Some experimental parameters are listed in Table 1, and some corresponding experimental results are listed in Table 2.

concentrations fed in the reactor. Reaction temperature is the temperature of oxidizing durene in the reactor.

TABLE 2

The corresponding experimental results of oxidizing durere and the results of purifying PMDA.

| Exp. No. | PMDA Yield of the 1st Cyclone separator inlet (wt %) | Product Purity (%) | | | | |
|---|---|---|---|---|---|---|
| | | 1st Cyclone Separator | | 2nd Cyclone Separator | | |
| | | PMDA | PMA | PMDA | PMA | Durene |
| 98 | 46.3 | 99.0+ | 0 | 75.6 | 0 | 0 |
| 109 | 65.0 | 99.0+ | 0 | 58.7 | 0 | 0 |
| 111 | 99.9 | 99.0+ | 0 | 83.6 | 0 | 0 |
| 112 | 87.8 | 99.0+ | 0 | 63.2 | 0 | 0 |
| 113 | 84.9 | 99.0+ | 0 | 81.3 | 0 | 0 |
| 114 | 75.3 | 99.0+ | 0 | 71.2 | 0 | 0 |
| 115 | 94.0 | 99.0+ | 0 | 81.9 | 0 | 0 |
| 118 | 89.5 | 99.0+ | 0 | 78.2 | 0 | 0 |
| 119 | 86.0 | 99.0+ | 0 | 68.7 | 0 | 0 |
| 120 | 89.9 | 99.0+ | 0 | 75.2 | 0 | 0 |
| 121 | 57.0 | 99.0+ | 0 | 59.6 | 0 | 0 |
| 122 | 78.8 | 99.0+ | 0 | 64.8 | 0 | 0 |
| 123 | 93.8 | 99.0+ | 0 | 74.5 | 0 | 0 |

Postscript: The purity of PMDA used to be an analyzing standard is 99%. There are no impurities found in PMDA obtained by this method according to the analyzing spectrum of both gas chromatography and liquid chromatography. The melting point of PMDA obtained by this method is the same as the pure PMDA as shown by the spectrum obtained from the Differential Thermal Analyzer. From all spectrum described above, the purity of PMDA obtained by this method is estimated to be much higher than 99.0% (about 99.9%).

From the data shown in Table 2, needle crystals of high-purity PMDA is directly obtainable from the first cyclone separator. No quenching gas or other purification steps are needed, and no PMA contamination is found. In the second cyclone separator, PMDA with lower-purity, which can be further purified, is also collected.

TABLE 1

Experimental parameters of oxidizing durene to PMDA.

| Experiment Number | Gases Space Flow Rate of Reactor ($hr^{-1}$) | Feed-In Conc. (mol %) | React. Temp. (° C.) | Temp. of the Reactor Outlet (° C.) | Gases Flow Rate of the 1st Cyclone Separator inlet (m/s) | Operating Temp. of the 1st Cyclone Separator (° C.) | Operating Temp. of the 2nd Cyclone Separator (° C.) |
|---|---|---|---|---|---|---|---|
| 98 | 6,000 | 0.30 | 340 | 250 | 15 | 170 | 140 |
| 109 | 6,000 | 0.27 | 350 | 250 | 15 | 190 | 40 |
| 111 | 6,000 | 0.33 | 343 | 250 | 15 | 210 | 160 |
| 112 | 6,000 | 0.36 | 340 | 250 | 10 | 175 | 120 |
| 113 | 6,000 | 0.34 | 343 | 250 | 15 | 175 | 120 |
| 114 | 6,000 | 0.34 | 343 | 250 | 20 | 175 | 120 |
| 115 | 6,000 | 0.33 | 343 | 250 | 15 | 175 | 160 |
| 118 | 6,000 | 0.28 | 348 | 250 | 15 | 180 | 135 |
| 119 | 6,000 | 0.33 | 348 | 250 | 15 | 180 | 110 |
| 120 | 6,000 | 0.32 | 343 | 250 | 15 | 180 | 140 |
| 121 | 5,000 | 0.36 | 348 | 250 | 15 | 160 | 70 |
| 122 | 7,000 | 0.26 | 348 | 250 | 15 | 160 | 100 |
| 123 | 6,000 | 0.33 | 343 | 250 | 15 | 160 | 120 |

Space flow rate is gas that passes per unit volume of catalyst in per unit time. Feed-In concentration is the reactant From the preferred embodiment, only simple purification steps can obtain high-purity PMDA (purity>99.0%). The complicated purification steps are largely simplified in this invention. The cost of producing high-purity PMDA is also largely decreased. Therefore, this invention is very suitable to be applied in mass-production of high-purity PMDA.

It will be apparent to those skilled in the art that various modifications and variations can be made to the method of the present invention without departing from the scope or spirit of the invention. In view of the foregoing, it is intended that the present invention cover modifications and variations of this invention provided they fall within the scope of the following claims and their equivalents.

What is claimed is:

1. A purification method for obtaining high-purity PMDA, which comprises:

connecting a reactor outlet with an inlet of a first cyclone separator in series, wherein the temperature of the reactor outlet is higher than a sublimation temperature of PMDA and the temperature of the first cyclone separator is lower than the sublimation temperature of PMDA and higher than that of by-products; and directing vapors of the PMDA and the by-products to flow from the reactor outlet to the inlet of the first cyclone separator at a flow rate to obtain high-purity PMDA in the first cyclone separator.

2. The purification method of claim 1, wherein the PMDA is an oxidation product of durene.

3. The purification method of claim 1, wherein a temperature of the reactor outlet is about 245 to about 255° C.

4. The purification method of claim 1, wherein a temperature of the first cyclone separator is about 165 to about 210° C.

5. The purification method of claim 1, wherein the flow rate is less than 20 m/s.

6. The purification method of claim 1, wherein the flow rate is about 15 m/s.

7. The purification method of claim 1, which further comprises connecting an outlet of the first cyclone separator with an inlet of a second cyclone separator and a temperature of the second cyclone separator is lower than the sublimation temperature of the by-products.

8. The purification method of claim 7, wherein the temperature of the second cyclone separator is about 110 to about 165° C.

9. The purification method of claim 7, which further comprises connecting an outlet of the second cyclone separator with an inlet of a third cyclone separator and a temperature of the third cyclone separator is lower than the sublimation temperature of the by-products.

10. The purification method of claim 9, wherein the temperature of the third cyclone separator is about 110 to about 165° C.

11. A purification method for obtaining high-purity PMDA, which is applicable to the oxidation of durene to gain PMDA and comprises:

connecting a reactor with a first cyclone separator in series, wherein the temperature of the reactor is about 245 to about 255° C. and the temperature of the first cyclone separator is about 165 to about 210° C.; and directing vapors of the PMDA and the by-products to flow from the reactor to the first cyclone separator at a flow rate to obtain PMDA with purity larger than 99.0% in the first cyclone separator.

12. The purification method of claim 11, wherein the flow rate is less than 20 m/s.

13. The purification method of claim 11, wherein the flow rate is about 15 m/s.

14. The purification method of claim 11, which further comprises connecting the first cyclone separator with more than one cyclone separator in series and a temperature of the cyclone separators is lower than the sublimation temperature of the by-products.

15. The purification method of claim 14, wherein the temperature of the cyclone separator is about 110 to about 165° C.

* * * * *